(12) United States Patent
Mueller

(10) Patent No.: US 10,722,348 B2
(45) Date of Patent: Jul. 28, 2020

(54) INTRAOCULAR LENS SUPPLY SYSTEM COMPRISING A HEATING ELEMENT

(71) Applicant: Carl Zeiss Meditec AG, Jena (DE)

(72) Inventor: Marco Mueller, Berlin (DE)

(73) Assignee: Carl Zeiss Meditec AG, Jena (DE)

( * ) Notice: Subject to any disclaimer, the term of this patent is extended or adjusted under 35 U.S.C. 154(b) by 148 days.

(21) Appl. No.: 15/920,672

(22) Filed: Mar. 14, 2018

(65) Prior Publication Data

US 2018/0200048 A1 Jul. 19, 2018

Related U.S. Application Data

(63) Continuation of application No. PCT/EP2016/071417, filed on Sep. 12, 2016.

(30) Foreign Application Priority Data

Sep. 14, 2015 (DE) .......................... 10 2015 217 495

(51) Int. Cl.
*A61F 2/16* (2006.01)
(52) U.S. Cl.
CPC ...... *A61F 2/1678* (2013.01); *A61F 2210/008* (2013.01)
(58) Field of Classification Search
CPC .... A61F 2/1662; A61F 2/1664; A61F 2/1667; A61F 2/167; A61F 2/1672; A61F 2/1675; A61F 2/1678; A61F 2/1681; A61F 2002/30088; A61F 2002/1682; A61F 2002/1683; A61F 2002/1681;
(Continued)

(56) References Cited

U.S. PATENT DOCUMENTS 5,263,991 A * 11/1993 Wiley .................. A61F 2/0095
126/263.06
8,900,249 B2 12/2014 Boukhny et al.
(Continued)

FOREIGN PATENT DOCUMENTS

CN 1113324 A 12/1995
CN 101573088 A 11/2009
(Continued)

OTHER PUBLICATIONS

English language translation of Office Action issued in German Patent Application No. DE 10 2015 217 495.6 (from which this application claims priority), dated Jun. 13, 2016.
(Continued)

*Primary Examiner* — Anh T Dang
(74) *Attorney, Agent, or Firm* — Falk Ewers; Ewers IP Law PLLC

(57) ABSTRACT

An intraocular lens supply system is provided. The intraocular lens supply system includes a housing and a cartridge. The cartridge is configured to receive an intraocular lens and can be inserted into the housing. The intraocular lens supply system further includes a heating element including a latent heat accumulator and a nucleating agent, and a pressure element which is coupled to the cartridge or the housing and which can be displaced such that the pressure element exerts a pressing force onto the nucleating agent when the cartridge is inserted into the housing in such a manner that thermal energy can be supplied to the cartridge from the heating element.

15 Claims, 3 Drawing Sheets

(58) Field of Classification Search
CPC ...... A61F 2002/1686; A61F 2002/1689; A61F 2002/169; A61F 2002/16902; A61F 2002/16901; A61F 2002/16903; A61F 2002/16905; A61F 2002/169051; A61F 2002/169052; A61F 2002/169053; A61F 2210/008
See application file for complete search history.

(56) References Cited

U.S. PATENT DOCUMENTS

| | | | |
|---|---|---|---|
| 2008/0097460 A1 | 4/2008 | Boukhny et al. | |
| 2008/0097461 A1* | 4/2008 | Boukhny | A61F 2/1678 606/107 |
| 2011/0264102 A1 | 10/2011 | Cole et al. | |
| 2011/0264103 A1 | 10/2011 | Cole et al. | |
| 2016/0074156 A1 | 3/2016 | Raquin et al. | |
| 2017/0042666 A1* | 2/2017 | Maroscheck | A61F 2/1691 |
| 2017/0231884 A1 | 8/2017 | Huang et al. | |

FOREIGN PATENT DOCUMENTS

| | | |
|---|---|---|
| CN | 204033812 U | 12/2014 |
| DE | 102013105185 A1 | 11/2014 |
| DE | 102014005719 A1 | 10/2015 |
| WO | 2008105965 A2 | 9/2008 |
| WO | 2015161837 A1 | 10/2015 |

OTHER PUBLICATIONS

Wikipedia Article "Latent heat storage unit" downloaded Jul. 5, 2015 at https://de.wikipedia.org/w/index.php?title=Latentw%C3%A4mespeicher&oldid=143750466.

International Search Report of the European Patent Office in PCT/EP2016/071417 (from which this application claims priority) dated Nov. 28, 2016.

International Preliminary Report on Patentability of the European Patent Office in PCT/EP2016/071417 (from which this application claims priority) dated Mar. 20, 2018 and English language translation thereof.

English-language translation of Office Action and Search report dated Aug. 2, 2019 issued in Chinese counterpart application No. 201680053288.

* cited by examiner

INTRAOCULAR LENS SUPPLY SYSTEM COMPRISING A HEATING ELEMENT

CROSS REFERENCE TO RELATED APPLICATIONS

This application is a continuation application of international patent application PCT/EP2016/071417, filed Sep. 12, 2016, designating the United States and claiming priority to German application 10 2015 217 495.6, filed Sep. 14, 2015, and the entire content of both applications is incorporated herein by reference.

TECHNICAL FIELD

The invention relates to an intraocular lens supply system.

BACKGROUND

There are multiple surgical techniques for treating a clouding of the eye lens, which is referred to as a cataract in medicine. The most widespread technique is phacoemulsification, in which a thin tube is introduced into the diseased lens and induced to make vibrations by ultrasound. As a result of the vibrations, the hard lens is broken up or emulsified into small particles, which can be aspirated through the tube with a pump. A rinsing fluid (irrigation fluid) is supplied during this process, with the aspiration of the particles and of the fluid taking place through an aspiration line connected to the tube. When the lens has been completely emulsified and removed, a new artificial lens can be inserted into the empty capsular bag, and a patient treated in this way can re-attain good vision.

The artificial lens, which is referred to as intraocular lens, is inserted by an intraocular lens supply system. The intraocular lens supply system has a cannula, through which the intraocular lens is advanced by a plunger and inserted into the capsular bag of the patient. To keep the injury to the cornea as limited as possible, the diameter of the cannula, for example being 1.6 mm, is very small. However, such a small diameter requires the intraocular lens to be conveyed through the cannula in a rolled-up state. In order to be able to roll-up the intraocular lens, the intraocular lens is made of a soft material, which is usually a polymer. The material selection firstly influences the ability of the intraocular lens to be rolled-up in a tight cannula; secondly, it influences the elasticity of the intraocular lens during the advance in the cannula. These properties depend significantly on the temperature of the material of the intraocular lens. A temperature that is too low can lead to tears in the intraocular lens during the advance in the cannula, while a temperature that is too high may cause a permanent deformation of the intraocular lens.

United States Patent Application Publication No. 2008/097460 describes a heatable intraocular lens supply system, by which a desired temperature for the intraocular lens can be obtained. To this end, it is necessary to provide electrical connections and an energy source. Because of contacting problems, the electrical connections may fail, and, as a result, the heating may completely fail. If the energy source is a battery, this may significantly increase the weight of the intraocular lens supply system. Moreover, the use duration of batteries is limited, and so it may happen that the energy supply reduces or is no longer available during an operation. If an energy source is provided outside of the intraocular lens supply system, electrical connection cables are required. These cables have a negative impact on the handling of the intraocular lens supply system. In order to obtain the desired temperature for the intraocular lens, a temperature setting and, possibly, a sensor system for reaching the target temperature are required. This significantly increases the technical outlay for an intraocular lens supply system. A closed-loop control of the desired temperature increases the technical outlay even more.

SUMMARY

It is an object of the invention to provide a heatable intraocular lens supply system which requires only little technical outlay, which consumes minimal energy, which avoids electrical contacting problems, and which can be handled in the same manner as a non-heatable intraocular lens supply system.

According to an aspect of the invention, the intraocular lens supply system includes:

a housing,
a cartridge for receiving an intraocular lens which is insertable into the housing,
a heating element which has a latent heat store and a nucleation agent,
a pressure element which is coupled to the cartridge or the housing and displaceable in such a way that the pressure element exerts a compressive force on the nucleation agent when the cartridge is inserted into the housing such that thermal energy can be supplied to the cartridge from the heating element.

A latent heat store can store thermal energy in a hidden, low-loss manner, with many repetition cycles and over a long period of time. In a latent heat store, the latent heat of fusion, heat of solution or heat of absorption is substantially greater than the heat it could store because of its normal specific heat capacity. In a latent heat store, use is made of the enthalpy of thermodynamic state changes. By way of example, "charging" of the latent heat store can be effectuated by melting certain materials, with these materials taking up large amounts of thermal energy (heat of fusion). Then, "discharging" is effectuated after an activation as solidifying, with the latent heat store re-emitting the large amount of heat taken up previously to its surroundings as solidification heat. However, undercooling of the melt is unwanted, and therefore, the nucleation agents are added to the latent heat store according to an aspect of the invention. The nucleation agents cause a crystallization just below the melting point.

The latent heat store can be a salt hydrate $M_n H_2 O$, such as $Na_2 SO_4 \cdot 10 H_2 O$ (32.5° C.) or $NaCl \cdot Na_2 SO_4 \cdot 10 H_2 O$ (32.4° C.). The latent heat store may also be an oversaturated solution of sodium acetate $Na(CH_3 COO)$ or NaOAc (58° C.).

According to an aspect of the invention, the intraocular lens supply system is an injector, which has a pressure element coupled to the cartridge or the housing and is displaceable in such a way that the pressure element exerts a force on the nucleation agent when the cartridge is inserted into the housing. In the case of the pressure element, the force on the nucleation agent should be dimensioned such that crystallization is triggered in the latent heat store and the latent thermal energy is released thereby. This can be achieved by a force of 30 to 50 N, for example, on the nucleation agent.

The pressure element may be pretensioned such that an operator of the intraocular lens supply system may release the compressive force by releasing the pretension and the compressive force is able to act on the nucleation agent. On the other hand, the pressure element can exert a static compressive force on the nucleation agent by a displacement effectuated by the operator, for example by translation or rotation. Here, it is possible for the compressive force to increasingly act on the nucleation agent while the cartridge is inserted into the intraocular lens supply system. The exertion of force then is necessarily effectuated during the process of inserting the cartridge into the intraocular lens supply system. However, in the case of a cartridge that has already been inserted into the intraocular lens supply system, i.e., in the case of a so-called pre-charged intraocular lens supply system, it is likewise possible for the compressive force to be exerted on the nucleation agent by the pressure element for the first time when the time for this appears expedient to the operator. This time may depend on the time duration within which the cartridge or the intraocular lens received therein reaches a desired temperature after triggering the crystallization.

According to an aspect of the invention, the pressure element is displaceable. Hence, it is possible to modify a position of the pressure element and consequently a relative orientation between the pressure element and the cartridge or between the pressure element and the housing. This means that it is also possible to modify the compressive force which the pressure element can exert on the nucleation agent. Should the necessary compressive force for triggering the crystallization of the nucleation agent not be sufficient, for example because of manufacturing inaccuracies of a cartridge, the force can easily be increased by displacing the pressure element. However, the displacement of the pressure element may also be advantageous if, in the case of a non-pre-charged intraocular lens supply system, the operator has difficulties inserting the cartridge into the housing. If the travel for the displacement of the pressure element is then reduced, for example, this causes a lower force for inserting the cartridge into the housing, whereupon a lower force is available for triggering the crystallization. Provided the crystallization is triggered, such a displaceable pressure element still is advantageous.

According to an exemplary embodiment, the heating element can be connected only to the cartridge. A single surface of the heating element may form a support area for the intraocular lens to be heated. The surface of the heating element can have a plane or arched, e.g., concave, embodiment. A concave surface is advantageous since it is possible to direct more heat into an inner region of the cartridge and hence to an intraocular lens received in the cartridge. In particular, the heating element may have surfaces protruding from the support area next to the latter, the protruding surfaces likewise being able to emit heat. In this way, it is possible to obtain even more uniform heating of the inner region of the cartridge and the intraocular lens received therein. Moreover, it is advantageous in the case of a heating element being connected to the cartridge, that the surface of the heating element forms a support area for the intraocular lens, such that the cartridge can be embodied with relatively small dimensions. Further, it is possible for an intermediate layer to be present between the heating element and the intraocular lens, the intermediate layer ensuring a uniform heat distribution of the heat emitted by the heating element in the direction toward the intraocular lens.

According to further exemplary embodiment, the heating element is only connected to the housing. As a result, the heating element is not connected to the cartridge. This facilitates a cartridge with very small dimensions, which has little mass and consequently can be heated very quickly by the heating element and can be handled easily.

If the heating element is connected to the housing and the cartridge is inserted into the housing, and only a small distance in the range of 0.001 to 0.5 mm exists between the cartridge and the heating element so that the thermal energy released by the heating element can provide good heating of the cartridge and the intraocular lens held therein. According to another aspect of the invention, there is no distance at all between the heating element and the cartridge by virtue of there being an areal contact between the cartridge and the heating element. This achieves an ideal heat transfer from the heating element to the cartridge.

The invention renders it possible to emit a predetermined amount of energy to the intraocular lens, with no electrical energy, no electrical contacts and no cables being required. Hence, the intraocular lens supply system according to an aspect of the invention can be handled just as well as a non-heatable intraocular lens supply system. Here, the technical outlay for the intraocular lens supply system according to the aspect of the invention is very low.

According to a further aspect of the invention, the pressure element is a projection at a leaf element of the cartridge. A cartridge may contain an intraocular lens in a not yet rolled-up or folded state. If an operator wishes to insert the intraocular lens into the eye to be treated, the operator can slightly roll up the intraocular lens by pivoting at least one leaf element that is arranged laterally at the cartridge; see FIGS. 14 to 17 of United States Patent Application Publication No. 2016/0074156, for example. This pivot movement only occurs when the insertion of the intraocular lens into the eye is imminent. If, according to an aspect of the invention, a projection is located at a leaf element of the cartridge, a force is exerted between the projection and the heating element, and consequently a crystallization in the latent heat store starts just before the stronger rolling-up and transport of the intraocular lens into the cannula of the intraocular lens supply system. As a result, the heat is released automatically and without the actuation of further apparatus elements at a temporally expedient moment, at which greater elasticity and formability of the lens are required.

According to a further aspect of the invention, the displaceable pressure element has a punch, by which a compressive force can be exerted on the nucleation agent. A punch facilitates a freely adjustable force on the nucleation agent. It allows a great adjustment travel, and, as a result, the punch in a retracted state does not interfere with the cartridge being inserted into the housing. The punch can be provided in addition to the plunger used to transport the intraocular lens through the cannula and into the eye. However, it is also possible for the punch to have an integral embodiment with the plunger for transporting the intraocular lens. The adjustment travel of the punch may be shorter than the adjustment travel of the plunger. The punch only serves to trigger the crystallization of the nucleation agent, and, as a result, the punch no longer advances further after this trigger of the crystallization of the heating element. By way of example, this can be effectuated by virtue of the punch decoupling from the plunger. If the punch no longer carries out a movement, only the plunger still moves to transport the intraocular lens when the operator actuates the plunger.

According to a further aspect of the invention, the housing has a displaceable housing part. This may be advantageous if the housing part can be grasped well by an operator, even with protective gloves, and this consequently allows a displacement to be achieved in a simple manner, for example in the form of a translational movement. This simplifies the handling of the intraocular lens supply system according to an aspect of the invention. Then, the pressure element is preferably coupled to the housing, with there being a displacement of the pressure element as a result of a displacement of the housing part.

According to another aspect of the invention, the heating element has a plurality of nucleation agents. If a force is exerted onto these nucleation agents in each case, it is possible to trigger a crystallization at a plurality of locations in the latent heat store. Hence, heat is released at a plurality of locations, and better heating of the cartridge and an intraocular lens held therein can be achieved. The nucleation agents may be arranged with a uniform distribution in the heating element. As a result, it is possible to obtain a uniform heating of the intraocular lens.

According to yet another aspect of the invention, the intraocular lens supply system has a component between the housing and the heating element, the component having a greater heat reflection or a greater heat insulation than the housing. The crystallization releases thermal energy which, initially, is not steered into a direction but which is emitted from the crystallization points in a spherical manner. If, according to this aspect of the invention, provision is made of a component which has a greater heat reflection or a greater heat insulation than the housing, the heat can be directed more strongly in the direction of the cartridge and the intraocular lens received therein, with relatively little heat being emitted into housing regions at a distance from the intraocular lens.

According to a further aspect of the invention, the heating element has a volume in the range of 150 to 500 mm$^3$, and the latent heat store releases thermal energy in the range of 50 to 300 joule, preferably 50 to 100 joule, after an activation of the nucleation agent. This facilitates the development of an intraocular lens supply system which has similar dimensions and similarly good handling as a non-heatable intraocular lens supply system.

BRIEF DESCRIPTION OF THE DRAWINGS

The invention will now be described with reference to the drawings wherein.

DESCRIPTION OF EXEMPLARY EMBODIMENTS

Figure 1:
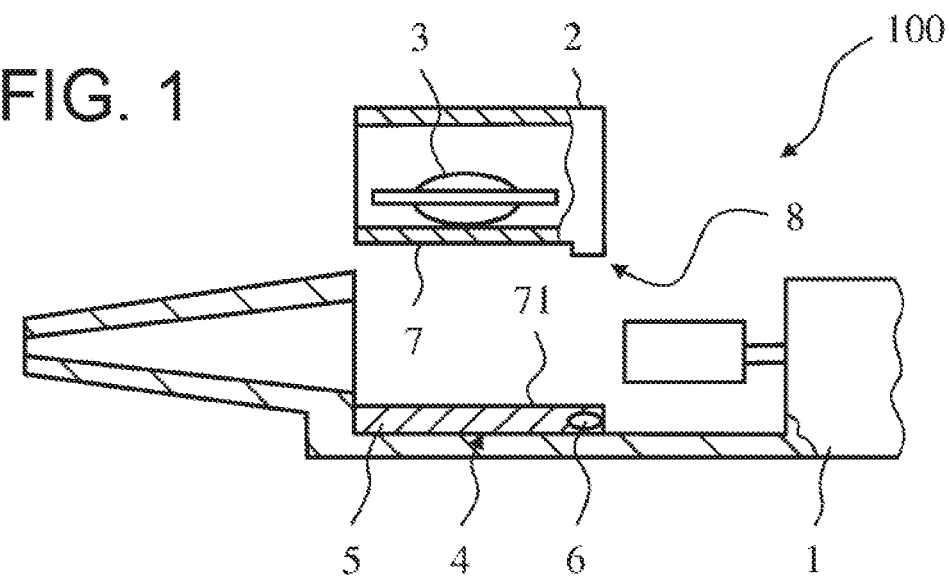
FIG. 1 shows a schematic illustration of a first exemplary embodiment of the intraocular lens supply system, with a cartridge that is not inserted into a housing.

FIG. 1 shows a schematic illustration of a first exemplary embodiment of the intraocular lens supply system 100. The intraocular lens supply system 100 has a housing 1 and a cartridge 2 that is insertable into the housing 1, for receiving an intraocular lens 3. In the exemplary embodiment illustrated in FIG. 1, the cartridge 2 has not yet been inserted into the housing 1. Further, the intraocular lens supply system 100 has a heating element 4 for heating the cartridge 2 and the intraocular lens 3 contained therein, when the cartridge 2 is inserted into the housing 1. It is clear from FIG. 1 that the heating element 4 is coupled to the housing 1. The housing 1 may have a guide rail which extends in the vertical or horizontal direction, for example, and which is suitable for engaging with a groove in the cartridge 2. The cartridge 2 can be inserted into the housing 1 by hand or by an apparatus provided in the housing 1. Inserting the cartridge 2 into the housing 1 means that the cartridge 2 is positioned in the vicinity of the heating element 4.

Figure 2:
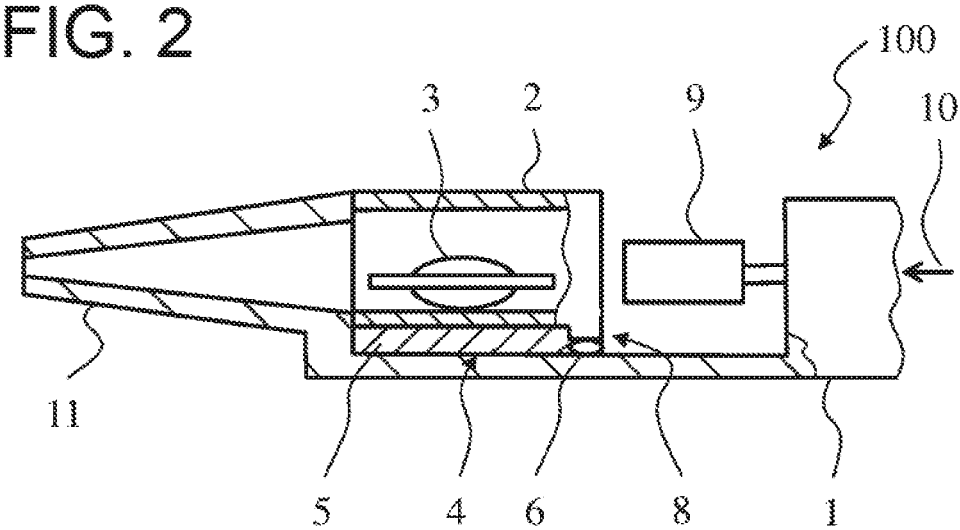
FIG. 2 shows a schematic illustration of the first exemplary embodiment of the intraocular lens supply system, wherein the cartridge is inserted into the housing.

The heating element 4 has a latent heat store 5 and a nucleation agent 6. If the cartridge 2 is inserted into the housing 1, a pressure element 8, which is coupled to the cartridge 2 in this exemplary embodiment, exerts a compressive force on the nucleation agent 6 of the heating element 4. This situation is shown in FIG. 2. The pressure element 8 acts on the heating element 4 with the nucleation agent 6 contained therein, with the lower side 7 of the cartridge 2 contacting the upper side 71 of the heating element 4. By exerting a compressive force on the nucleation agent 6 by way of the pressure element 8, a crystallization can be triggered in the latent heat store 5, as a result of which thermal energy is guided from the latent heat store 5 to the cartridge 2 and the intraocular lens 3 received therein. Once the intraocular lens 3 has been sufficiently heated by the supplied thermal energy, it is possible to guide the intraocular lens 3 in the direction of a cannula 11 of the intraocular lens supply system 100 by a plunger 9, the position of which is changeable in an advance direction along the arrow 10. The cannula 11 has a substantially conical shape, and so the intraocular lens 3 is rolled-up in this cannula 11 with an increasing forward motion of the plunger 9. In order to obtain little heat loss, the heating element 4 is only arranged directly under the cartridge 2. However, it is also possible for the cannula 11 to be heated as well.

The latent heat store 5 may be arranged in a heating element 4 with a cuboid shape, with the heating element 4 having dimensions for length×height×width of 20 mm×10 mm×1.25 mm, for example. If sodium sulfate is used as material for the latent heat store 5, thermal energy in the range of approximately 60 to 70 joule may be released in the case of these dimensions. If a heat transfer coefficient between the heating element 4 and the cartridge 2 inserted into the housing 1 of approximately 200 W/(m$^2$·K) is assumed, the thermal energy can reach the cartridge 2 and, there, the intraocular lens 3 from the heating element 4 within approximately 1 minute in order to heat these elements.

Figure 3:
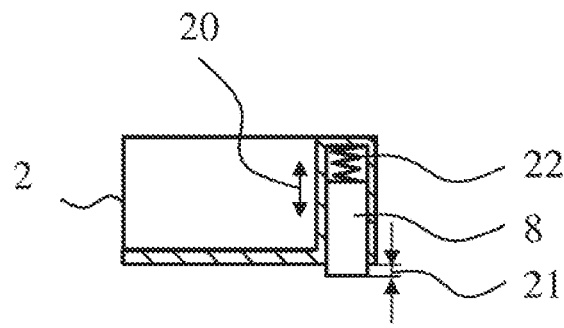
FIG. 3 shows a schematic illustration of a cartridge for the first exemplary embodiment of the intraocular lens supply system.

According to the first exemplary embodiment of the intraocular lens supply system 100, the cartridge 2 is provided with a displaceable pressure element 8, as illustrated in FIG. 3. The pressure element 8 can be displaced in terms of its position in the vertical direction along the double-headed arrow 20, for example by a thread (not illustrated in FIG. 3), and thereby a modifiable distance 21 relative to the lower side 7 of the cartridge is achieved 2. By using this approach, it is easily possible to compensate for manufacturing inaccuracies, and it is always possible to obtain a desired distance 21 for the contact with the heating element 4 and the nucleation agent 6 situated therein. The pressure element 8 can be pretensioned by a spring 22, which can be released by an operator when the crystallization of the nucleation agent is triggered. Hence, not only a static compressive force, but also a collision is triggered on the nucleation agent 6, and a start of the crystallization can be effectuated very reliably. In general, provision can be made of a mechanical, electrical, magnetic or chemical energy store to accelerate the pressure element 8 such that the latter can strike the nucleation agent 6 with impact energy.

Figure 4:
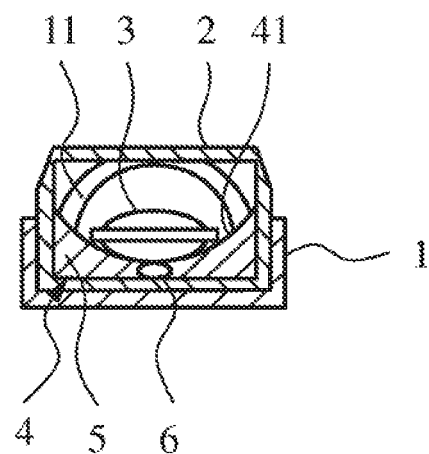
FIG. 4 shows a schematic cross-sectional view of the intraocular lens supply system according to a second exemplary embodiment.

FIG. 4 shows a cross-sectional view of the intraocular lens supply system according to a second exemplary embodiment with a cartridge 2 inserted into the housing 1, with a section transversely to the advance direction 10 being illustrated. The intraocular lens 3 lies directly on a surface 41 of the heating element 4, with the heating element 4 being connected to the cartridge 2. The surface 41 has a concave shape, and so thermal energy emitted by the heating element 4 is oriented well in the direction toward the intraocular lens 3.

Figure 5:
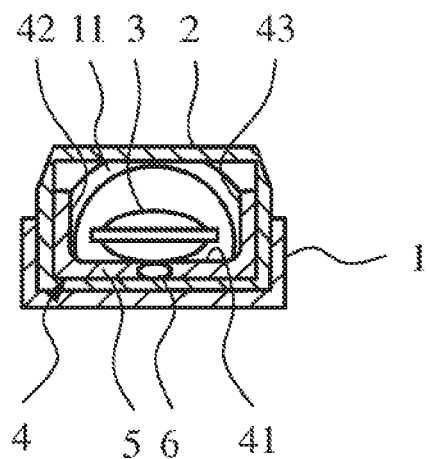
FIG. 5 shows a schematic cross-sectional view of the intraocular lens supply system according to a third exemplary embodiment.

FIG. 5 shows a cross-sectional view of the intraocular lens supply system according to a third exemplary embodiment with a cartridge 2 inserted into the housing 1, with a section transversely to the advance direction 10 being illustrated. The heating element 4, which is likewise connected to the cartridge 2 in this case, has such a shape that it has a plane support area 41 for the intraocular lens 3 and, adjacent to the support area 41, surfaces 42 and 43 that project perpendicular from the latter, said surfaces likewise being able to emit heat. In this way, it is possible to obtain relatively uniform heating of the inner region of the cartridge 2 and the intraocular lens 3 received therein.

Figure 6:
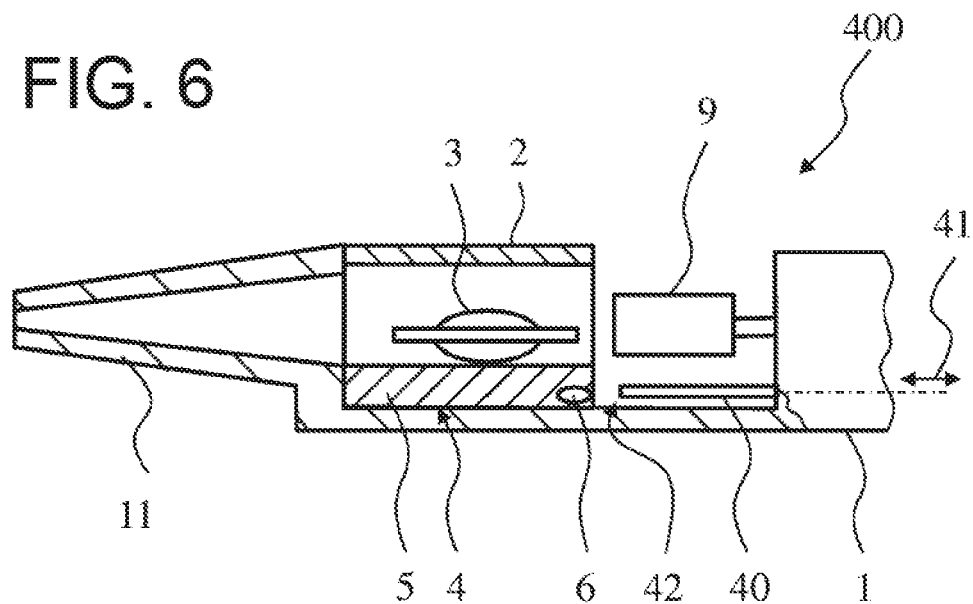
FIG. 6 shows a schematic illustration of a fourth exemplary embodiment of the intraocular lens supply system with a displaceable punch.

FIG. 6 shows a fourth exemplary embodiment of an intraocular lens supply system 400, in which the cartridge 2 is not provided with the pressure element 8 according to the first exemplary embodiment. A punch 40 is provided as a displaceable pressure element in this intraocular lens supply system 400. The punch 40 is movably guided in the direction of the double-headed arrow 41. By displacing the punch 40 in the direction toward the heating element 4, a compressive force can be exerted on the nucleation agent 6 by a tip 42 of the punch 40 and a crystallization of the nucleation agent 6 can be triggered. In this exemplary embodiment, the heating element 4 is connected to the cartridge 2. However, the heating element 4 can also be connected to the housing 1.

The punch 40 can be coupled to the plunger 9 or it can be movable independently of the plunger 9. Coupling the punch 40 and plunger 9 is advantageous as consequently only the plunger 9, for example, needs to be actuated by an operator. After reaching the required compressive force for triggering the crystallization of the nucleation agent 6, the punch 40 may decouple in the case of a further advance of the plunger 9, after which there is only an advance of the plunger 9 and the intraocular lens 3.

Figure 7:
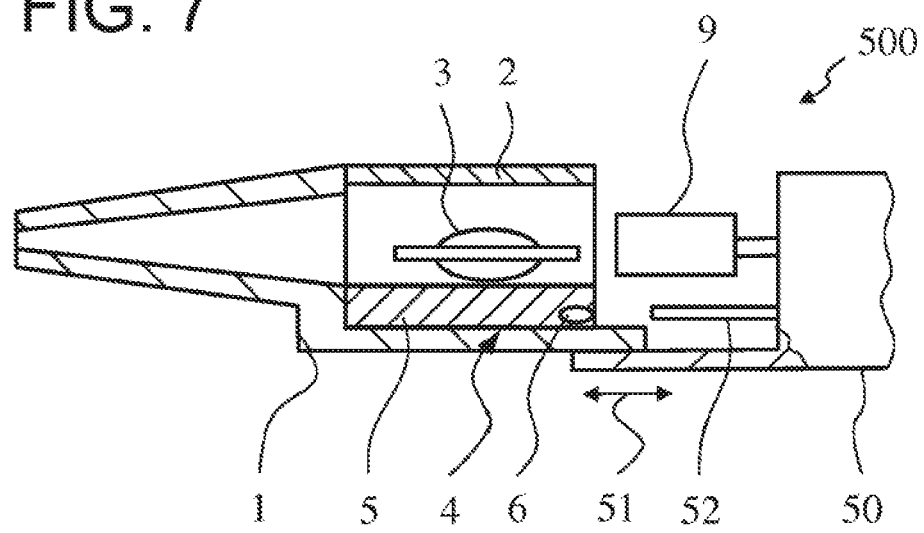
FIG. 7 shows a schematic illustration of a fifth exemplary embodiment of the intraocular lens supply system with a displaceable housing part.

FIG. 7 illustrates a fifth exemplary embodiment of an intraocular lens supply system 500. Here, the intraocular lens supply system 500 has a housing part 50, which is a constituent part of the housing 1, said housing part 50 being displaceable in the direction of the double-headed arrow 51. If this housing part 50 has a pressure element in the form of a projection 52, for example as a punch 40 that is rigidly coupled to the housing part 50, it is possible to exert a force on the nucleation agent 6 by way of a horizontal displacement of the housing part 50. Subsequently, the plunger 9 can be actuated in the advance direction 10 to convey the intraocular lens 3 to the cannula 11. In this exemplary embodiment, the heating element 4 is connected to the cartridge 2. However, the heating element 4 can also be connected to the housing 1.

It is understood that the foregoing description is that of the exemplary embodiments of the invention and that various changes and modifications may be made thereto without departing from the spirit and scope of the invention as defined in the appended claims.

What is claimed is:

1. An intraocular lens supply system comprising:
    a housing including a cannula and a plunger, the plunger being configured to transport an intraocular lens through the cannula into an eye;
    a cartridge insertable into the housing and configured to receive the intraocular lens;
    a heating element including a latent heat store and a nucleation agent; and
    a pressure element coupled to at least one of the cartridge and the housing and being displaceable to exert a compressive force on the nucleation agent when the cartridge is inserted into the housing to supply thermal energy to the cartridge from the heating element.

2. The intraocular lens supply system as claimed in claim 1, wherein the housing has a displaceable housing part.

3. The intraocular lens supply system as claimed in claim 1, wherein the heating element includes a plurality of nucleation agents.

4. The intraocular lens supply system as claimed in claim 1, further comprising a component arranged between the housing and the heating element, the component having at least one of a heat reflection that is greater than the heat reflection of the housing and a heat insulation that is greater than the heat insulation of the housing.

5. The intraocular lens supply system as claimed in claim 1, wherein the heating element has a volume in a range of from 150 to 500 mm$^3$ and the latent heat store releases thermal energy in a range of from 50 to 300 joule after activation of the nucleation agent.

6. An intraocular lens supply system comprising:
    a housing;
    a cartridge insertable into the housing and configured to receive an intraocular lens;
    a heating element including a latent heat store and a nucleation agent; and
    a pressure element coupled to at least one of the cartridge and the housing and being displaceable to exert a compressive force on the nucleation agent when the cartridge is inserted into the housing to supply thermal energy to the cartridge from the heating element,
    wherein the pressure element is a projection at a leaf element of the cartridge.

7. The intraocular lens supply system as claimed in claim 6, wherein the housing has a displaceable housing part.

8. The intraocular lens supply system as claimed in claim 6, wherein the heating element includes a plurality of nucleation agents.

9. The intraocular lens supply system as claimed in claim 6, further comprising a component arranged between the housing and the heating element, the component having at least one of a heat reflection that is greater than the heat reflection of the housing and a heat insulation that is greater than the heat insulation of the housing.

10. The intraocular lens supply system as claimed in claim 6, wherein the heating element has a volume in a range of from 150 to 500 mm$^3$ and the latent heat store releases thermal energy in a range of from 50 to 300 joule after activation of the nucleation agent.

11. An intraocular lens supply system comprising:
a housing;
a cartridge insertable into the housing and configured to receive an intraocular lens;
a heating element including a latent heat store and a nucleation agent; and
a pressure element coupled to at least one of the cartridge and the housing and being displaceable to exert a compressive force on the nucleation agent when the cartridge is inserted into the housing to supply thermal energy to the cartridge from the heating element,
wherein the pressure element has a punch.

12. The intraocular lens supply system as claimed in claim 11, wherein the housing has a displaceable housing part.

13. The intraocular lens supply system as claimed in claim 11, wherein the heating element includes a plurality of nucleation agents.

14. The intraocular lens supply system as claimed in claim 11, further comprising a component arranged between the housing and the heating element, the component having at least one of a heat reflection that is greater than the heat reflection of the housing and a heat insulation that is greater than the heat insulation of the housing.

15. The intraocular lens supply system as claimed in claim 11, wherein the heating element has a volume in a range of from 150 to 500 $mm^3$ and the latent heat store releases thermal energy in a range of from 50 to 300 joule after activation of the nucleation agent.

* * * * *